US006193373B1

(12) United States Patent
Apple et al.

(10) Patent No.: US 6,193,373 B1
(45) Date of Patent: Feb. 27, 2001

(54) EYE ILLUMINATION SYSTEM AND METHOD

(75) Inventors: Howard P. Apple, Winter Park; Martin P. Nevitt, Oviedo; Xiaofeng Han, Orlando, all of FL (US)

(73) Assignee: LaserSight Technologies, Inc., Winter Park, FL (US)

( * ) Notice: Subject to any disclaimer, the term of this patent is extended or adjusted under 35 U.S.C. 154(b) by 0 days.

(21) Appl. No.: 09/472,951

(22) Filed: Dec. 27, 1999

Related U.S. Application Data (63) Continuation of application No. 09/176,755, filed on Oct. 22, 1998, now Pat. No. 6,007,202.
(60) Provisional application No. 60/062,696, filed on Oct. 23, 1997.

(51) Int. Cl.[7] .......................................................... A61B 3/10
(52) U.S. Cl. .......................................................... 351/221
(58) Field of Search ........................... 351/205, 209–212, 351/221, 246, 208; 393/422

(56) References Cited

U.S. PATENT DOCUMENTS

| 2,480,737 | 8/1949 | Jayle . |
| 3,074,407 | 1/1963 | Moon . |
| 3,476,112 | 11/1969 | Elstein . |
| 3,697,889 | 10/1972 | Dewey, Jr. . |
| 3,743,965 | 7/1973 | Offner . |
| 3,848,104 | 11/1974 | Locke . |
| 3,938,058 | 2/1976 | Yamamoto . |
| 3,966,310 | * 6/1976 | Larson .................................. 351/221 |
| 3,982,541 | 9/1976 | L'Esperance, Jr. . |

(List continued on next page.)

FOREIGN PATENT DOCUMENTS

| 1243732 | 10/1984 | (CA) . |
| 0151869A2 | 8/1985 | (EP) . |
| 0296982A1 | 6/1988 | (EP) . |
| 0368512A2 | 5/1990 | (EP) . |
| 0207648A2 | 8/1990 | (EP) . |
| 0418890A3 | 3/1991 | (EP) . |
| 0602756A1 | 6/1994 | (EP) . |
| PCT/FR87/00139 | 11/1987 | (WO) . |
| PCT/US92/09625 | 5/1993 | (WO) . |
| PCT/US93/00327 | 8/1993 | (WO) . |
| PCT/US94/02007 | 9/1994 | (WO) . |
| PCT/EP95/01287 | 10/1995 | (WO) . |

OTHER PUBLICATIONS

Qiushi Ren, Raymond P. Galitis, Keith P. Thompson, & J. T. Lin, "Ablation of the Cornea and Synthetic Polymers Using a UV (213 nm) Solid State Laser", IEEE Journal of Quatum Electronics, Dec. 1990, pp. 2284–2288.

Conference on Lasers and Electro–Optics, Optical Society of America, May 1990, pp. 28–30.

G.P.A. Malcom, M.A. Persaud, & A.I. Ferguson, "Resonant Frequency Quadrupling of a Mode—Locked Diode—Pumped Nd: YLF Laser", Optics Letters, Jul. 1991, pp. 983–985.

(List continued on next page.)

*Primary Examiner*—George Manuel
(74) *Attorney, Agent, or Firm*—William H. Bollman (57) ABSTRACT

A system for illuminating an eye useful for tracking movement of an eye during vision correction treatments includes a generally arcuate main body having. The main body is constructed and arranged to be mounted in spaced relation to an eye to be tracked. An infrared light source is carried by the main body on at least a significant portion of its inner circumferential surface to direct infrared light toward the eye being treated at an angle from about 20 to 45 degrees with respect to an iris base plane of the eye being tracked.

21 Claims, 5 Drawing Sheets

U.S. PATENT DOCUMENTS

| | | |
|---|---|---|
| 3,983,507 | 9/1976 | Tang et al. . |
| 4,169,663 | 10/1979 | Murr . |
| 4,180,751 | 12/1979 | Ammann . |
| 4,349,907 | 9/1982 | Campillo et al. . |
| 4,386,428 | 5/1983 | Baer . |
| 4,423,728 | 1/1984 | Lieberman . |
| 4,461,294 | 7/1984 | Baron . |
| 4,477,159 | 10/1984 | Mizuno et al. . |
| 4,520,816 | 6/1985 | Schachar et al. . |
| 4,526,171 | 7/1985 | Schachar . |
| 4,538,608 | 9/1985 | L'Esperance, Jr. . |
| 4,546,773 | 10/1985 | Kremer et al. . |
| 4,573,467 | 3/1986 | Rich et al. . |
| 4,580,559 | 4/1986 | L'Esperance, Jr. . |
| 4,598,714 | 7/1986 | Kremer et al. . |
| 4,619,259 | 10/1986 | Graybill et al. . |
| 4,633,866 | 1/1987 | Peyman et al. . |
| 4,641,349 * | 2/1987 | Flom et al. .......................... 351/205 |
| 4,653,495 | 3/1987 | Nanaumi . |
| 4,662,370 | 5/1987 | Hoffman et al. . |
| 4,665,913 | 5/1987 | L'Esperance, Jr. . |
| 4,669,466 | 6/1987 | L'Esperance, Jr. . |
| 4,688,570 | 8/1987 | Kramer et al. . |
| 4,718,418 | 1/1988 | L'Esperance, Jr. . |
| 4,720,189 | 1/1988 | Heyman et al. . |
| 4,721,379 | 1/1988 | L'Esperance, Jr. . |
| 4,729,372 | 3/1988 | L'Esperance, Jr. . |
| 4,729,373 | 3/1988 | Peyman . |
| 4,732,148 | 3/1988 | L'Esperance, Jr. . |
| 4,755,043 * | 7/1988 | Carter .................................. 351/205 |
| 4,764,930 | 8/1988 | Bille et al. . |
| 4,770,172 | 9/1988 | L'Esperance . |
| 4,773,414 | 9/1988 | L'Esperance, Jr. . |
| 4,784,135 | 11/1988 | Blum et al. . |
| 4,798,204 | 1/1989 | L'Esperance, Jr. . |
| 4,807,623 | 2/1989 | Lieberman . |
| 4,838,266 | 6/1989 | Koziol et al. . |
| 4,838,679 | 6/1989 | Bille . |
| 4,840,175 | 6/1989 | Peyman . |
| 4,848,340 | 7/1989 | Bille et al. . |
| 4,856,513 | 8/1989 | Muller . |
| 4,862,886 | 9/1989 | Clarke et al. . |
| 4,896,015 | 1/1990 | Taboada et al. . |
| 4,903,695 | 2/1990 | Warner et al. . |
| 4,907,586 | 3/1990 | Bille et al. . |
| 4,911,711 | 3/1990 | Telfair et al. . |
| 4,925,523 | 5/1990 | Braren et al. . |
| 4,941,093 | 7/1990 | Marshall et al. . |
| 4,968,130 | 11/1990 | Hideshima et al. . |
| 4,975,918 | 12/1990 | Morton . |
| 4,993,826 | 2/1991 | Yoder . |
| 4,994,058 | 2/1991 | Raven et al. . |
| 5,019,074 | 5/1991 | Muller . |
| 5,048,946 | 9/1991 | Sklar et al. . |
| 5,052,004 | 9/1991 | Gratze et al. . |
| 5,063,942 | 11/1991 | Kilmer et al. . |
| 5,065,046 | 11/1991 | Guyer . |
| 5,074,859 | 12/1991 | Koziol . |
| 5,102,409 | 4/1992 | Balgorod . |
| 5,108,388 | 4/1992 | Trokel . |
| 5,108,412 | 4/1992 | Krumeich et al. . |
| 5,133,726 | 7/1992 | Ruiz et al. . |
| 5,144,630 | 9/1992 | Lin . |
| 5,163,934 | 11/1992 | Munnerlyn . |
| 5,163,936 | 11/1992 | Black et al. . |
| 5,182,759 | 1/1993 | Anthon et al. . |
| 5,188,631 | 2/1993 | L'Esperance, Jr. . |
| 5,196,006 | 3/1993 | Klopotek et al. . |
| 5,207,668 | 5/1993 | L'Esperance, Jr. . |
| 5,217,452 | 6/1993 | O'Donnell . |
| 5,219,343 | 6/1993 | L'Esperance, Jr. . |
| 5,219,344 | 6/1993 | Yoder, Jr. . |
| 5,222,960 | 6/1993 | Poley . |
| 5,226,903 | 7/1993 | Mizuno . |
| 5,250,062 | 10/1993 | Hanna . |
| 5,257,988 | 11/1993 | L'Esperance, Jr. . |
| 5,263,950 | 11/1993 | L'Esperance, Jr. . |
| 5,284,477 | 2/1994 | Hanna et al. . |
| 5,288,292 | 2/1994 | Giraud et al. . |
| 5,290,301 | 3/1994 | Lieberman . |
| 5,312,320 | 5/1994 | L'Esperance, Jr. . |
| 5,312,393 | 5/1994 | Mastel . |
| 5,324,281 | 6/1994 | Muller . |
| 5,334,190 | 8/1994 | Seiler . |
| 5,336,217 | 8/1994 | Buys et al. . |
| 5,345,281 | 9/1994 | Taboada et al. . |
| 5,345,534 | 9/1994 | Najm et al. . |
| 5,345,543 * | 9/1994 | Najm et al. .......................... 392/422 |
| 5,349,590 | 9/1994 | Amirkhanian et al. . |
| 5,350,374 | 9/1994 | Smith . |
| 5,353,262 | 10/1994 | Yakymyshyn et al. . |
| 5,360,424 | 11/1994 | Klopotek . |
| 5,363,388 | 11/1994 | Shi et al. . |
| 5,364,388 | 11/1994 | Koziol . |
| 5,370,641 | 12/1994 | O'Donnell, Jr. . |
| 5,395,356 | 3/1995 | King et al. . |
| 5,395,362 | 3/1995 | Sacharoff et al. . |
| 5,405,355 | 4/1995 | Peyman et al. . |
| 5,411,501 | 5/1995 | Klopotek . |
| 5,423,801 | 6/1995 | Marshall et al. . |
| 5,425,727 | 6/1995 | Koziol . |
| 5,425,729 | 6/1995 | Ishida et al. . |
| 5,437,658 | 8/1995 | Muller et al. . |
| 5,441,511 | 8/1995 | Hanna . |
| 5,442,487 | 8/1995 | Mizuno . |
| 5,445,633 | 8/1995 | Nakamura et al. . |
| 5,461,212 | 10/1995 | Seiler et al. . |
| 5,463,430 * | 10/1995 | Isogai et al. .......................... 351/208 |
| 5,470,329 | 11/1995 | Sumiya . |
| 5,474,548 | 12/1995 | Knopp et al. . |
| 5,480,396 | 1/1996 | Simon et al. . |
| 5,505,723 | 4/1996 | Muller . |
| 5,507,741 | 4/1996 | L'Esperance, Jr. . |
| 5,507,799 | 4/1996 | Sumiya . |
| 5,520,679 | 5/1996 | Lin . |
| 5,541,419 | 7/1996 | Arackellian . |
| 5,549,597 | 8/1996 | Shimmick et al. . |
| 5,556,395 | 9/1996 | Shimmick et al. . |
| 5,582,608 | 12/1996 | Brown . |
| 5,582,752 | 12/1996 | Zair . |
| 5,599,340 | 2/1997 | Simon et al. . |
| 5,613,965 | 3/1997 | Muller . |
| 5,624,436 | 4/1997 | Nakamura et al. . |
| 5,634,920 | 6/1997 | Hohla . |
| 5,637,109 | 6/1997 | Sumiya . |
| 5,646,791 | 7/1997 | Glockler . |
| 5,651,784 | 7/1997 | Klopotek . |
| 5,668,622 | 9/1997 | Charbonnier et al. . |
| 5,683,379 | 11/1997 | Hohla . |
| 5,684,562 | 11/1997 | Fujieda . |
| 5,711,762 | 1/1998 | Trokel . |
| 5,713,892 | 2/1998 | Shimmick . |
| 5,735,843 | 4/1998 | Trokel . |
| 5,782,822 | 7/1998 | Telfair et al. . |
| 5,849,006 | 12/1998 | Frey et al. . |
| 5,865,830 | 2/1999 | Parel et al. . |

OTHER PUBLICATIONS

J.T. Lin, J.L. Montgomery, "Temperaure—Tuned Noncritically Phase—Matched Frequency Conversion in $LiB_3O_5$ Crystal", Optics Communications, Dec. 1990, pp. 159–165.

A.A. Babin, F.I. Fel'dshtein, & I.V. Yakovlev, "Generation of the Fifth Harmonic of Yttrium Orthoaluminate: $Nd^{3+}$ Laser Radiation in KDP at Room Temperatures", Soviet Technical Physics Letters, Jun. 1990, pp. 417–418.

V.D. Volosov & E.V. Nilov, "Effect of the Spatial Sructure of a Laser Beam on the Generation of the Second Harmonic in ADP and KDP Crystals", UDC, Nov. 1965, pp. 715–719.

A.G. Arutyunyan, G.G. Gurzadyan, & R.K. Ispiryan, "Generation of the Fifth Harmonic of Picosecond Yttrium Aluminate Laser Radiation", Soviet Journal Quantum Electron, Dec. 1989, pp. 1602–1603.

Shinichi Imai, Toshitaka Yamada, Yasutomo Fujimori & Ken Ishikawa, Third—Harmonic Generation of an Alexandrite Laser in $\beta$–$BaB_2O_4$, Applied Physics Letters, May 1989, pp. 1206–1208.

Conference on Lasers and Electro–Optics, Optical Society of America, Apr. 1989, p. 390.

Barraquer, "Lamellar Keratoplasty (special techniques)" Annals of Ophthalmology, Jun. 1972, pp. 437–469.

Burnett, "Company Denies Delay in Approval for Laser", Orlando Sentinel, Feb. 1993, pp. 12–13.

Burnett, "Medical Technology", Orlando Sentinel, Feb. 1993, pp. 1–5.

Gaillitis et al., "Solid State Ultraviolet Laser (213 nm) Ablation of the Cornea and Synthetic Collagen Lenticules", Lasers in Surgery and Medicine, Dec. 1991, pp. 556–562.

Gartry et al., "Excimer Laser Photorefractive Keratectomy", Ophthalmology, Aug. 1992, pp. 1210–1219.

Gilbert, "Corneal Topography: In Search of the Excimer Islands", Eye Care Technology, Oct. 1993, pp. 23–28.

L'Esperance, "New Laser Systems, Their Potential Clinical Usefulness, and Investigative Laser Procedures", Ophthalmic Lasers, 1989, pp. 995–1045.

Lin et al, "Corneal Topography Following Excimer Photorefractive Kerectomy for Myopia", Journal of Cataract Refractive Surgery, 1993, pp. 149–154.

Lin et al, "A Multiwavelength Solid State Laser for Ophthalmic Applications", Ophthalmic Technolgies, Jun. 1992, pp. 266–275.

Marguerite B. McDonald et al, "Central Photorefractive Keratectomy for Myopia", Ophthalmology, Sep. 1991, pp. 1327–1337.

Marshall et al, "Long–term Healing of the Central Cornea after Photorefractive Keratectomy Using an Excimer Laser", Oct. 1998, pp. 1411–1421.

Marshall et al, "Photoablative Reprofiling of the Cornea Using an Excimer Laser: Photorefractive Keratectomy", Lasers in Ophthalmology, Jan. 1986, pp. 21–48.

McDonald et al., "Central Photorefractive Keratectomy for Myopia", Arch Ophthalmology, Jun. 1990, pp. 799–808.

Palikaris et al, "Excimer Laser in Situ Keratomileusis and Photorefractive Keratectomy for Correction of High Myopia", Journal of Refractive and Corneal Surgery, Sep. 1994, pp. 498–510.

Ren et al, "Corneal Refractive Surgery Using an Ultra–Violet (213nm) Solid State Laser" Ophthalmic Technologies, Jun. 1991, pp. 129–139.

Rozakis, "Refractive Lamellar Keratoplasty" History of Keratomileusis, 1994, Chapt. 1–13.

Seiler et al, "Excimer Laser (193nm) Myopic Keratomileusis in Sighted and Blind Human Eyes" Refractive and Corneal Laser Surgery, Jun. 1990, pp. 165–173.

Steinert et al, "Laser Corneal Surgery", Laser Research Laboratory, 1998, pp. 151–154.

Thompson et al, "Philosophy and Technique for Excimer Laser Phototheraputic Keratectomy", Refractive and Corneal Surgery, Apr. 1993, pp. 81–85.

Trokel et al Excimer Laser Surgery of the Cornea, American Journal of Ophthalmology, Dec. 1983, pp. 710–715.

Trockel et al, "Evolution of Excimer Laser Corneal Surgery", Jul. 1989, pp. 373–381.

Van Mielaert et al, "On the Safety of 193–Nanometer Excimer Laser Refractive Corneal Surgery" Refractive and Corneal Surgery, Jun. 1992, pp. 235–239.

Wilson et al, "Changes in Corneal Topography after Excimer Laser Photorefractive Keratectomy for Myopia", Ophthalmology, Sep. 1991, pp. 1338–1347.

\* cited by examiner

EYE ILLUMINATION SYSTEM AND METHOD

This application claims priority from Provisional Application 60/062,696, flied on Oct. 23,1997, entitled "Eye Tracker Lighting System for Laser Vision Correction"and Cont. application of Ser. No. 09/176,755, filed on Oct. 22, 1998, now U.S. Pat. No. 6,007,202.

BACKGROUND OF THE INVENTION

1. Field of the Invention

This invention relates to a lighting system for illuminating the eye and more particularly to a lighting system for video based tracking and correcting for eye movement during vision correction treatments.

2. Description of Related Art

Pupil position data obtained by eye tracking systems is used to detect eye motion during vision correction treatments. Conventional video based eye tracking systems automatically recognize and track the position of eye positions based on landmarks present within an image of a human eye. Such equipment requires illumination of the eye by infrared (IR) light. IR light typically 850 to 930 nanometers (nm) is used because it provides a good picture contrast between the pupil and iris. Additionally, the use of IR light decouples this lighting source from other visual sources which do not contain the infrared wavelengths.

The eye, illuminated by invisible IR light, is scanned by an infrared sensitive video camera. Under normal conditions, the pupil of the eye appears as a dark hole to the illumination. The dark pupil image is input to a real-time eye tracking system consisting of a digital image processor that outputs pupil size and position coordinates relative to the scan of the camera. The eye tracking system includes a circuit and processor designed to acquire and track the dark pupil position even in the presence of shadows or other clutter normally found in images of the eye.

Figure 1:
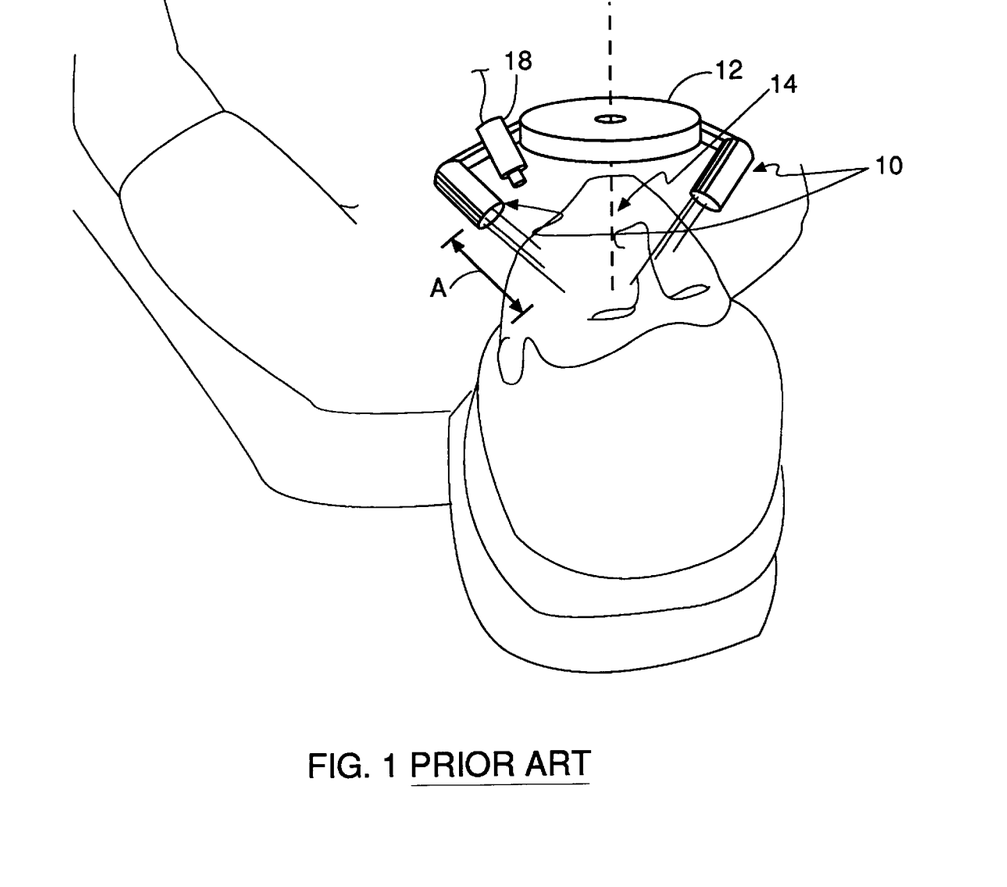
FIG. 1 is a perspective view of a conventional lighting system for illuminating the eye during vision correction treatment, shown disposed above an eye being treated.

FIG. 1 shows a conventional eye tracking system including illumination of the eye during laser vision correction surgery. The conventional illumination system includes one or two infrared light bundles 10, mounted on a central hub 12, to illuminate the eye for tracking by the eye tracking system. The path of a visible light beam used during vision correction treatments is shown at 14. A camera 18, sensitive to IR illuminations and fixed with respect to the subject's head, scans the eye to provide a video image for tracking the position of the eye.

Conventional illumination systems such as that shown in of FIG. 1 require that light bundles 10 be relatively close to the eye in order to achieve an evenly distributed illumination. Generally, the light bundles 10 are about 80 millimeters (mm) from the eye being treated, as shown by the dimension A in FIG. 1. This narrow spacing is a significant disadvantage because the light bundles 10 may interfere with the physician's hands either prior to or during the actual vision correction treatment. Additionally, the physician's hands can inadvertently block light emitted from one or both of the light bundles 10 causing a system efficacy and/or safety problem. Under certain circumstances, the patient's brow or nose can block light emitted from the light bundles 10 causing uneven illumination of the eye.

Additionally, conventional illumination systems such as that shown in FIG. 1 require the light bundles 10 to be within 0 to +/−20 degrees to the visual axis in order to achieve generally presumption of an even illumination. If not, the light bundles 10 must be painstakingly adjusted for each patient at the time of treatment to achieve the best possible illumination based on the shape of that particular patient's face, eyes, etc. This is a time-consuming process and may result in errors.

Figure 2:
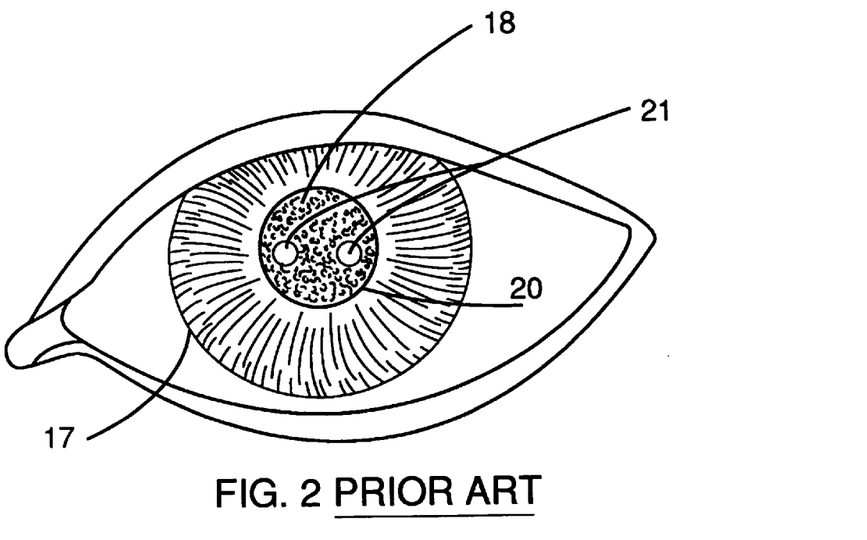
FIG. 2 is an enlarged plan view of specular reflections which occur on a pupil of an eye being illuminated with the conventional system of FIG. 1.
Figure 3:
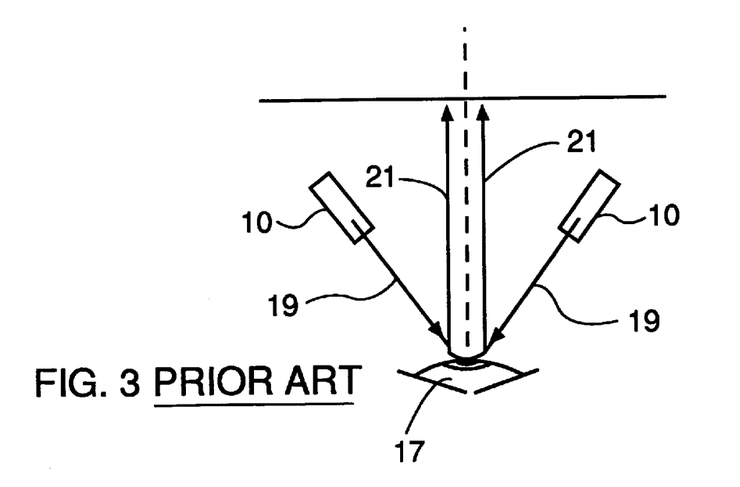
FIG. 3 is an elevation view of specular reflections which occur on an eye being illuminated with the conventional system of FIG. 1.

However, even if the light bundles 10 are positioned within the conventionally preferred 0 to +/−20 degrees to the visual axis, there is an additional problem caused by specular reflections. FIGS. 2 and 3 show specular reflections 21 at an eye 17 caused by any illumination system composed of point sources, e.g. light bundles 10. Because of the relatively narrow angle (0 to +/−20 degrees) at which the light beams 19 (FIG. 3) are delivered, the specular reflections 21 can occur either within the pupil 18 or even worse at the pupil/iris border 20. This makes the machine vision computer task of defining the pupil/iris border 20 much more complex and error prone.

The system shown in FIG. 1 was originally designed for research studies of normal eyes in which the epithelium is intact with a tear layer providing distinct specular reflections. These conditions no longer hold true for current laser vision correction techniques. In particular, either the epithelium is removed under a technique called surface Photorefractive Keratectomy (PRK), or a flap is cut with a microkeratome, the flap is folded back, and the treatment is performed on the underlying stromal layer (called LASIK). Both LASIK and PRK markedly affect Illumination for eye tracking systems. The eye, rather than being shiny and smooth, becomes dryer and more diffusely reflective. This often leads to additional time-consuming physician adjustment of the light bundles 10 during a critical time period of the surgery.

Another problem exists with conventional eye tracking lighting systems when used with laser vision correction treatments. An ablating laser beam dries and roughens the eye surface further obscuring the camera's view of the pupil/iris border 20 and the peripheral limbal border. Empirically, this disadvantageous effect is accentuated by relatively coaxial lighting provided by singular light sources placed close to the eye at angles of less that +/−20 degrees.

SUMMARY OF THE INVENTION

It is an object of the invention to provide a lighting system for illuminating the eye during vision correction treatments that does not physically interfere with preoperative and postoperative procedures, requires little or no physical adjustment, is insensitive to inadvertent light blockage, and minimizes or eliminates disadvantageous specular reflections at the pupil/iris border. These objects are attained in accordance with the principles of the present invention by providing a method and system which includes a generally arcuate main body. The main body is constructed, and arranged to be mounted in spaced relation to an eye to be tracked. An infrared light source is carried by the main body on at least a portion of its inner circumferential surface to direct infrared light toward the eye being treated at an angle from about 20 to 45 degrees with respect to an iris base plane of the eye being tracked.

BRIEF DESCRIPTION OF THE DRAWINGS

Features and advantages of the present invention will become apparent to those skilled in the art from the following description with reference to the drawings, in which.

DETAILED DESCRIPTION OF THE INVENTION

Figure 4:
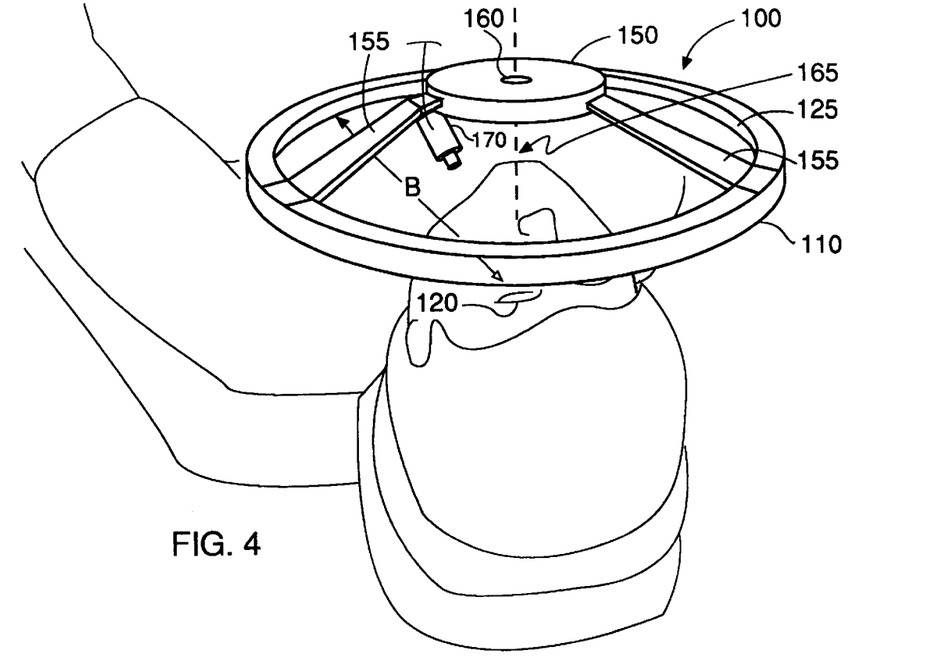
FIG. 4 is a perspective view of a lighting system for illuminating the eye during laser vision correction treatment provided in accordance with the principles of a first embodiment the invention and shown disposed above an eye being treated.

With reference to FIG. 4, a first embodiment of an eye illumination system is shown, generally indicated at 100, which embodies the principles of the present invention.

Figure 5:
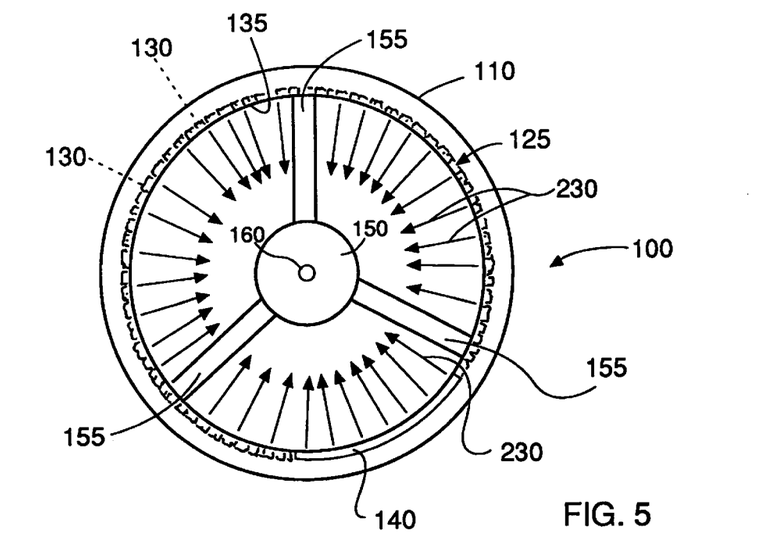
FIG. 5 is a plan view of the lighting system of FIG. 4, showing light sources in the form of a light pipe or in the form of a plurality of light emitters

The eye illumination system 100 includes an illuminating device in the form of a generally arcuate main body 110 constructed and arranged to be mounted in spaced relation to an eye being treated. As shown in FIG. 5, the main body 110 is in the form of a continuous ring having an inner diameter generally sufficient to ensure that adequate space is provided above the patient's face for the surgeon to maneuver. It has been determined that an inner diameter greater that about 140 mm is sufficient to ensure adequate space for maneuverability.

In the illustrated embodiment, the inner diameter of the ring-shaped main body 110 is approximately 280 mm. This 280 mm diameter permits the main body 110 to be disposed away from the eye 120 a distance of approximately 165 mm, as shown by the dimension B in FIG. 4. The main body 110 includes an infrared light source 125 for directing infrared light towards the eye being treated. The light source 125 may comprise a plurality of infrared light emitters 130 (FIG. 5) that are evenly or randomly spaced along an inner circumferential surface 135 of the main body 110. The light emitters 130 may be fiber bundles, light emitting diodes, lasers, electro luminescent panels, etc. It has been determined that for the disclosed embodiment 180 light emitters 130 spaced evenly about the inner circumferential surface 135 provides sufficient illumination, although more or less light emitters 130 may be employed. Further, the number of light emitters 130 may be reduced by eliminating light emitters 130, e.g., at the 3, 6, 9, and/or 12 o'clock locations, without noticeable illumination degradation. Eliminating light emitters in these regions also simplifies eye tracker measurements.

Alternatively, the light source 125 may be an infrared light pipe 140 disposed on the inner circumferential surface 135, a portion of which is shown in FIG. 5. The light pipe 140 is preferably provided along the entire inner circumferential surface 135, but may be disposed only along significant portions thereof.

In the illustrated embodiment, a hub or mount 150 is coupled to the main body 110 by a plurality of spokes 155 so that the hub 150 is generally concentric with the ring-shaped main body 110. The hub may be used for mounting the main body 110 to a fixed location and/or for mounting a visible light source (not shown) thereto. The hub 150 includes a passage 160, through which a visible light beam 165 may be delivered to the eye 120 being treated.

An eye imaging camera 170 (FIG. 4) may be provided in the conventional manner to scan the eye 120. The camera 170 may be connected to a conventional pupil tracking system, such as, for example, the RK-416PC Pupil Tracking System manufactured by ISCAN INC. of Cambridge, Mass. This conventional ISCAN Tracking System comprises a real time digital image processor that automatically tracks the center of the patient's pupil and measures pupil size and pupil position from a video image of the patient's eye. Another example of an eye imaging camera and digital imaging system that may be employed with an eye illumination system in accordance with the principles of the present invention is disclosed in U.S. Pat. No. 5,684,562, the content of which is hereby incorporated into the present specification by reference.

In operation, the eye is illuminated with a low-level (preferably 850 to 930 nm) infrared eye illumination source according to the principles of the invention. The pupil acts a sink to the IR light and while surrounding areas of the pupil reflect the IR light back to the camera 170, yielding dark pupil eye images. A bright corneal reflection corresponds to the reflection of the IR light off of the cornea. The eye imaging camera 170 is fitted with an optics package having an infrared pass filter to obtain a clear, in-focus image of the eye.

Figure 6:
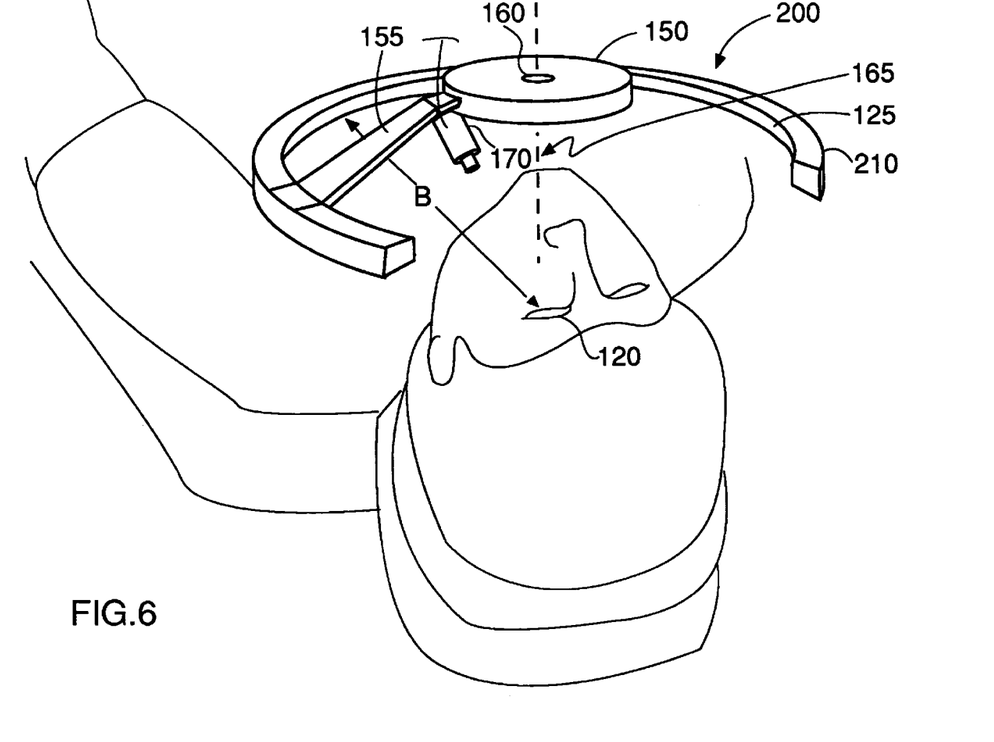
FIG. 6 is a perspective view of a lighting system for illuminating the eye during laser vision correction treatment provided in accordance with the principles of a second embodiment of the invention and shown disposed above an eye being treated.

With reference to FIG. 6, a second embodiment of an eye illumination system of the present invention is shown generally at 200. The main body 210 is of the second embodiment is generally C-shaped. All other components of the eye illumination system 200 are as described with respect to the eye illumination system 100 shown in FIG. 4.

The inner diameter of the main body 210 is preferably greater than about 140 mm, as in the first embodiment of the invention. The embodiment shown in FIG. 6 has an inner diameter of about 280 mm. The C-shaped main body 210 has an open portion 220 to allow an unobstructed view for the physician. The C-shaped main body 210 is typically configured with respect to the patient such that the open region is toward the top of the patient's head, where illumination is typically blocked by the patient's brow. Thus, even though the embodiment of FIG. 6; does not encompass a full 360 degrees, there is generally no compromise in eye illumination.

Figure 7:
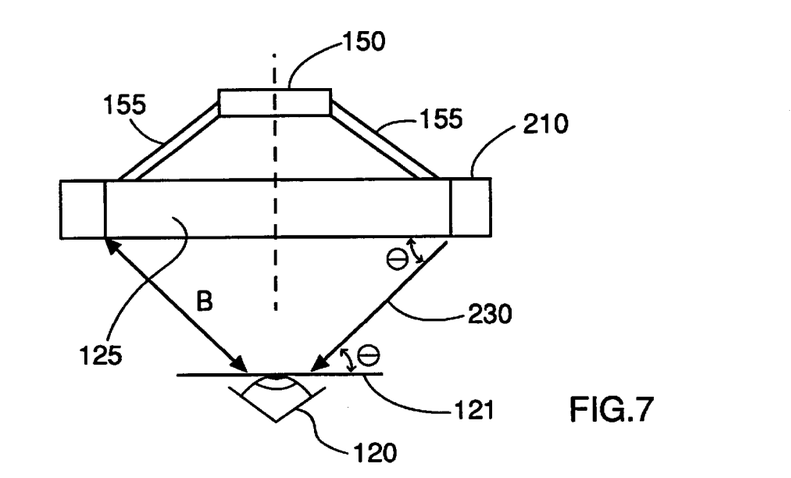
FIG. 7 is an elevation view of the lighting system of FIG. 6 shown disposed above an eye to be treated.

With the eye illumination system in accordance the principles of the present invention, as shown in FIG. 7, light rays 230 are emitted towards the eye at an angle θ which is approximately between 20 to 45 degrees, and preferably between 25 to 40 degrees to an iris base plane 121. The iris base plane 121 is considered to be the plane which is tangential to the outer edge of the iris.

Figure 8:
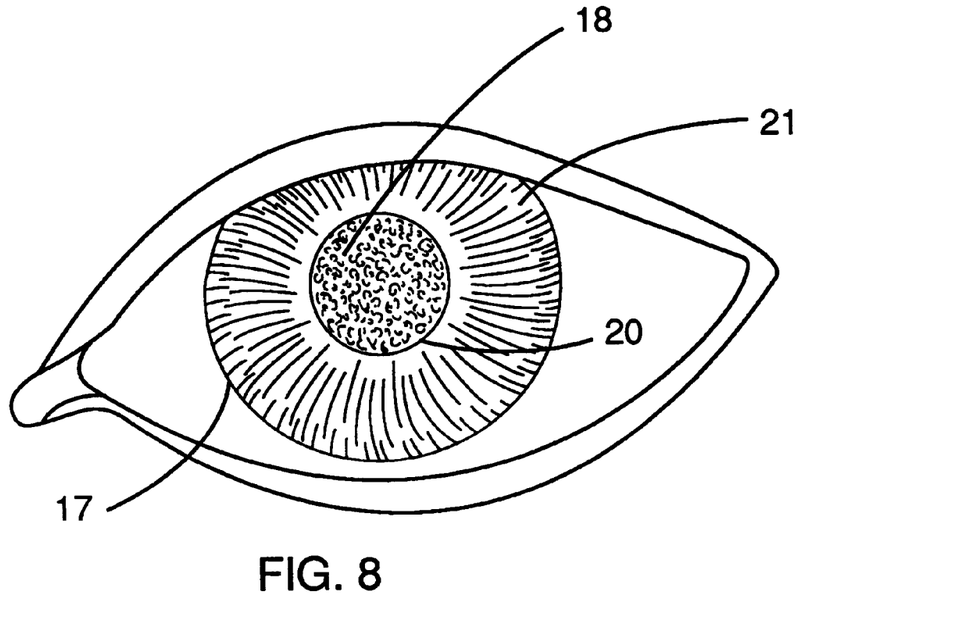
FIG. 8 is a plan view of an eye showing the location of specular reflections outside the pupil/iris border, which result from the lighting system of the invention.

As shown in FIG. 8, an illumination system in accordance with the principles of the present invention eliminates specular reflections at the pupil/iris border 20. Thus, eye tracking performance can be improved significantly.

The main body of a ring-shaped or C-shaped eye illumination system works equally well in treating left and right eyes with no adjustment. The lights become automatically centered under conventional laser vision correction centering methods. Thus, advantageously, no further adjustment of the eye illumination system is required during surgery.

With an eye illumination system in accordance wit the principles of the present invention, the main body may be mounted sufficiently distance from the patient's face so as to not interfere with the physician's hands. If a physician's hand should inadvertently block some of the light from the eye illumination system, there is sufficient light from other portions of the main body to achieve adequate and even illumination of the eye.

Moreover, the infrared light beams are directed at a sufficiently oblique angle such that specular reflections caused by the light source do not interfere with the pupil/iris border, particularly during eye movement encountered during patient fixation. This leads to greater increased accuracy and reliability of eye tracking.

It can be appreciated that the eye illumination system of the present invention provides an effective way of illuminating an eye, particularly for the purposes of tracking and correcting eye movements during vision correction treatments. Since the eye illumination system is constructed and arranged to be significantly spaced from the patient's face, there is less likelihood of the physician' 5 hand interfering with the overall light source. Further, the angle at which the light is directed to the eye ensures that specular reflection interference at the iris/pupil border is minimized or eliminated.

While the invention has been described in accordance with what is presently considered to be the preferred embodiments, it is to be understood that the invention is not limited to the disclosed embodiments, but on the contrary, is intended to cover various modifications and equivalent arrangements included within the spirit and scope of the appended claims.

What is claimed is:

1. An eye illumination system comprising:
    a main body; and
    one or more clusters of light sources distributed on said main body;
    said main body being constructed such that light from said one or more clusters of light sources is directed to a pupil of an eye to be illuminated at an angle between 20 degrees and 45 degrees with respect to a plane tangential to an iris of said eye.

2. The eye illumination system according to claim 1, wherein:
    light from said one or more clusters of light sources is directed to said pupil of said eye at an angle greater than 25 degrees with respect to a plane tangential to an iris of said eye.

3. The eye illumination system according to claim 1 wherein:
    said one or more clusters of light sources are infrared light sources.

4. The eye illumination system according to claim 1 wherein:
    said clusters of light sources include a plurality of light emitters.

5. The eye illumination system according to claim 1, further comprising:
    a hub member; and
    and at least one spoke coupling said hub member to said main body.

6. The eye illumination system according to claim 1, in combination with:
    an eye imaging device to receive light from said one or more clusters of light sources reflected from said eye.

7. An eye illumination system comprising:
    a main body;
    one or more clusters of light sources distributed on said main body;
    said main body being constructed such that light from said one or more clusters of light sources is directed to a pupil of an eye to be illuminated at an angle between 20 degrees and about 45 degrees with respect to a plane tangential to an iris of said eye.

8. An eye illumination system comprising:
    a main body;
    one or more clusters of light sources distributed on said main body;
    said main body being constructed such that light from said one or more clusters of light sources is directed to a pupil of an eye to be illuminated at an angle between 20 degrees and about 40 degrees with respect to a plane tangential to an iris of said eye.

9. An eye illumination system comprising:
    a mount; and
    one or more clusters of light sources distributed on said mount;
    said mount being constructed and arranged to be fixed in spaced relation to an eye to be illuminated such that light from said one or more clusters of light sources is directed to a pupil of said eye at an angle between 20 degrees and 45 degrees with respect to a plane tangential to an iris of said eye.

10. The eye illumination system according to claim 9, wherein:
    each of said one or more clusters of lights sources are infrared light sources.

11. An eye illumination system comprising:
    a mount;
    one or more clusters of light sources distributed on said mount;
    said mount being constructed and arranged to be fixed in spaced relation to an eye to be illuminated such that light from said one or more clusters of light sources is directed to a pupil of said eye at an angle greater than 20 degrees and less than about 45 degrees with respect to a plane tangential to an iris of said eye.

12. An eye illumination system comprising:
    a mount;
    one or more clusters of light sources distributed on said mount:
    said mount being constructed and arranged to be fixed in spaced relation to an eye to be illuminated such that light from said one or more clusters of light sources is directed to a pupil of said eye at an angle light from said one or more clusters of light sources between about 25 degrees and 40 degrees with respect to a plane tangential to an iris of said eye.

13. A method of illuminating an eye, comprising:
    providing one or more clusters of light sources; and
    mounting said one or more clusters of light sources in spaced relation from an eye being illuminated such that light from said one or more clusters of light sources is directed toward a pupil of said eye at an angle between 25 degrees and 45 degrees with respect to a plane tangential to an iris of said eye.

14. The method of illuminating said eye according to claim 13, further comprising:

spacing said one or more clusters of light sources greater than about 165 mm from said eye.

15. A method of illuminating an eye, comprising:

providing one or more clusters of light sources; and mounting said one or more clusters of light sources in spaced relation from an eye being illuminated such that light from said one or more clusters of light sources is directed toward a pupil of said eye at an angle between about 25 degrees and 40 degrees with respect to a plane tangential to an iris of said eye about 40 degrees with respect to a plane tangential to an iris of said eye.

16. A method of illuminating an eye, comprising:

providing one or more clusters of light sources;

mounting said one or more clusters of light sources in spaced relation from an eye being illuminated such that light from said one or more clusters of light sources is directed toward a pupil of said eye at an angle greater than about 25 degrees with respect to a plane tangential to an iris of said eye; and spacing said one or more clusters of light sources greater than about 100 mm from said eye.

17. A method of illuminating and tracking a position of an eye, said method comprising:

illuminating a pupil of an eye with one or more clusters of light sources from a distance of at least about 100 mm and at an angle of between 20 degrees and 45 degrees; and tracking a position of said pupil of said eye with an eye tracking system.

18. The method of illuminating and tracking the position of an eye according to claim 17, wherein:

said step of illuminating said pupil of said eye spaces said one or more clusters of light sources at least about 165 mm from said pupil of said eye.

19. The method of illuminating and tracking the position of an eye according to claim 17, wherein:

said step of illuminating said pupil of said eye directs said illumination of said pupil of said eye at an angle greater than about 25 degrees.

20. A method of illuminating and tracking a position of an eye, said method comprising:

illuminating a pupil of an eye with one or more clusters of light sources from a distance of at least about 100 mm and at an angle of greater than 20 degrees; and tracking a position of said pupil of said eye with an eye tracking system;

wherein said step of illuminating said pupil of said eye directs said illumination of said pupil of said eye at an angle less than about 45 degrees.

21. A method of illuminating and tracking a position of an eye, said method comprising:

illuminating a pupil of an eye with one or more clusters of light sources from a distance of at least about 100mm and at an angle of greater than 20 degrees; and tracking a position of said pupil of said eye with an eye tracking system;

wherein said step of illuminating said pupil of said eye directs said illumination of said pupil of said eye at an angle less than about 40 degrees.

* * * * *